United States Patent [19]
Logan et al.

[11] Patent Number: 5,313,968
[45] Date of Patent: May 24, 1994

[54] JOINT RANGE OF MOTION ANALYZER USING EULER ANGLE

[75] Inventors: Samuel E. Logan; Paul G. Groszewski, both of St. Louis, Mo.

[73] Assignee: Washington University, St. Louis, Mo.

[21] Appl. No.: 512,868

[22] Filed: Apr. 23, 1990

[51] Int. Cl.$^5$ .................................................. A61B 5/11
[52] U.S. Cl. .............................. 128/782; 73/1 E
[58] Field of Search ............... 128/774, 779, 782; 324/207, 247; 33/504, 511–515, 534; 73/1 E

[56] References Cited

U.S. PATENT DOCUMENTS

| | | | |
|---|---|---|---|
| 4,037,480 | 7/1977 | Wagner | 73/432 R |
| 4,571,834 | 2/1986 | Fraser et al. | 33/1 PT |
| 4,618,822 | 10/1986 | Hansen | 324/207 |
| 4,922,925 | 5/1990 | Crandall et al. | 128/782 |
| 4,986,280 | 1/1991 | Marcus et al. | 128/774 |
| 5,042,505 | 8/1991 | Mayer et al. | 128/781 |
| 5,082,003 | 1/1992 | Lamb et al. | 128/782 |

OTHER PUBLICATIONS

"Upper Extremity Kinematics Assessment Using Four Coupled Six Degree of Freedom Sensor" by S. E. Logan, P. Groszewski, J. C. Krieg and M. Vannier, from ISA Proceedings 1988.

*Primary Examiner*—Angela D. Sykes
*Attorney, Agent, or Firm*—Rogers, Howell & Haferkamp

[57] ABSTRACT

A joint range of motion evaluation system includes a three-dimensional orientation device which generates Euler angle (azimuth, elevation, roll) data closely corresponding to the permitted angular ranges of motion for many joints in a patient's body. Thus, the system collects angular data corresponding to the same angular movements experienced through the joint to provide greater information with regard to its actual movement. This information is particularly useful in detecting abnormalities and disabilities of movement and in designing and monitoring patient rehabilitation. Specific positional data with respect to specific points on the patient's joint or other surrounding anatomy is not utilized.

4 Claims, 3 Drawing Sheets

JOINT RANGE OF MOTION ANALYZER USING EULER ANGLE

BACKGROUND AND SUMMARY OF THE INVENTION

Clinical evaluation of a patient's extremities, and more particularly the upper extremities including the hands, for disability can be a time-consuming process for skilled therapists and physicians. Because of the unique complexity of the hands' movements, multiple measurements must be taken across all joints of the fingers to determine their maximum angle of flexion and extension. There are fourteen joints or knuckles in a normal hand, and each of these must be measured in flexion and extension to arrive at a measure of the disability of the hand as is often required for proper clinical evaluation and for the patient to obtain compensation for an injury which has limited his range of motion. At present, a therapist must sit with a patient and manually measure each individual angle of flexion and extension for each joint with a goniometer by isolating the joint, aligning it with the legs of the goniometer, and manually recording the measured included angle. Not only is this process tedious and time-consuming, and thus expensive to perform, but less time remains for the therapist to perform physical therapy with the patient. During the course of a patient's treatment, it is desirable to repeat these measurements over the time course of therapy to assess a patient's progress. Unfortunately, because there is some subjective element in the use of the goniometer and the current standard technique used in making hand function measurements, the repeatability of any particular examination is relatively poor. The variance of measurements from therapist to therapist has been so large with the standard goniometer that the same therapist should measure the same patients for each evaluation session. This is often not possible in a busy therapy center. This leads to uncertainty and ineffectiveness in assessing the patient's functional status and in designing treatment protocols.

Some attention has been paid in the prior art to the problem of evaluating and measuring the range of motion in the knee. Examples of these are found in U.S. Pat. Nos. 4,549,555 and 4,571,834. These references both contain the same disclosure relating to a knee laxity evaluator comprised of an instrumented seat, a restraint for restraining the thigh of the patient to the instrumented seat, a motion module consisting of a mechanical coupling extending between the seat and the patient's leg with a number of electromechanical rotary transducers for measuring the relative position of the leg, and a processor for analyzing the outputs of the seat and the motion modules to provide an indication of applied force and relative motion of the knee. The device disclosed is mechanically and operationally complex and is limited in its accuracy although it is probably adequate as measuring knee motion of a knee joint which is a very large joint whereas measuring finger motion requires much more delicate instrumentation.

Perhaps because of the bulky, mechanically complex construction of the device disclosed in these prior patents, the inventors herein are aware of a later commercial model of this device which is adapted for use with the spine which is comprised of a wand mounted at the end of a multi-jointed mechanical arm, the arm being adjustably mounted to a pole stand and having a rotary transducer at each of the joints of the arm. Apparently, a foot switch is also provided and the device is understood to be used by tracing an exterior outline corresponding to the perceived position of posterior elements and spinous processes in the spine with the wand as the foot switch is operated to input data corresponding to the shape of the spine to a computer which then performs an analysis including flexibilty and range of motion measurement. However, as with the prior art device disclosed in the patents mentioned above, the overall accuracy is limited by the use of the three rotary mono-angular (mono-articulated) single DOF transducers in the multi-jointed extension arm which are believed to generate only relative position data obtained by integrating a plurality of measurements over time, although the level of accuracy attainable is probably more than adequate for the measurement of the posterior elements of the dorsal and lumbar spine.

The inventors herein are also aware of a prior art device consisting of a "data glove" as is described generally in U.S. Pat. No. 4,542,291 and also in a *Scientific American* magazine article appearing on the cover and within the October 1987 issue. This device is essentially comprised of a glove which is slipped onto and encloses the hand and which contains a plurality of fiber-optic cables anchored at both ends to an interface board which run the length of each finger and doubles back. As the hand is measured, it is not visible to the operator. Each cable has a light-emitting diode at one end and a phototransistor at the other with the cables being treated so that light escapes when a finger flexes. Thus, a change in the amount of light received by the phototransistor, when converted into an electrical signal, is directly representative of a change in position or flexion of the finger such that the data glove can measure relative movement of the finger as it is flexed or extended. Additionally, an absolute position and orientation sensor is mounted near the wrist of the glove to provide a single absolute point of reference for the entire hand, although it does not provide data as to the position or angle of flexion or extension of any of the fingers themselves. The data glove provides simultaneous real time measurements concerning the relative motion or movement of the fingers but does not provide data corresponding to the absolute position of any of the fingers. Thus, to measure an angle of maximum flexion at each joint, the finger must first be placed in a known position and then the finger flexed to its position of maximum flexion as the output of the data glove is continuously monitored. The maximum angle of flexion may then be determined by comparing this known starting position with the angle of flexion computed by integrating continuously recorded measurements. Of course, there is some uncertainty in determining and repeating a known initial position and angle for a finger before it is flexed, especially if that finger is incapable of a full and complete range of motion. Once again, as with the prior art manual technique, and the rotary transducers of the prior art knee device, significant potential for error and subjectivity enter into the measurement of angles of flexion and extension with the data glove. There is no provision for competent human intervention in the operation of the data glove.

Still another problem in evaluating the hand is the complex nature of the wrist. Presently, in accepted standards of medical practice, the range of motion for the wrist is determined by having the patient grip a cylindrical object such as a pencil or the like, and holding the pencil in a vertical orientation which is defined as a neutral position. The patient is then told to rotate the pencil inwardly to its maximum extent and the angle is measured, and then to rotate the pencil outwardly to its maximum extent and that angle is measured as well. These angular measurements can then be used to determine the maximum pronation and supination. However, it is known that there is approximately 30° of additional total rotation contained in the joints between the radius and ulna and the fingers such that these measurements are not the true measurements of the range of motion of the wrist. Thus, there exists no protocol or methodology in the prior art to properly fully evaluate the true range of motion of the wrist. Furthermore, none of the prior art devices discussed above are capable of generating data which accurately provides the range of motion for the wrist. This is partially due to the fact that it is difficult to visualize the radius and ulna as the wrist is rotated, and for the further reason that the prior art systems have errors of measurement which are significant in measuring the small distances which through the wrist rotates.

To solve these and other problems in the prior art, the assignee herein is also the assignee of U.S. Pat. No. 4,922,925, issued May 8, 1990, which discloses an upper extremity evaluation system which is particularly adapted to and useful in measuring the range of flexion and extension of the joints of the hand, wrist and elbow and automatically calculating a degree of disability in accordance with American Medical Association (AMA) standards commonly used by the courts and workers compensation boards in determining the financial compensation due to a patient for an injury. In a distinct departure from the prior art, that device adapts a three-dimensional spatial absolute position and orientation sensor into a computer measurement system which permits the convenient collection of data by a therapist corresponding to the absolute position of the proximal and distal segments at a joint in the fully extended as well as the fully flexed position. In other words, a therapist can quickly and conveniently enter data automatically into the computer which corresponds to the (x, y, z) position of the various joints of the patient's hand as the hand is manipulated into one of only several different positions and held for only a brief period of time therein. Because absolute (x, y, z) position data is measured and collected, much greater accuracy is attainable. Furthermore, because of the convenient methodology used to collect the data, an evaluation is also capable of a high level of repeatability. This has a dramatic impact on the accuracy of the initial assessment given to a patient, as well as the evaluation of treatment protocols through the course of the patient's rehabilitation. Still another advantage with that system is that accurate range of motion information can be easily collected by measuring the exact location of the radial and ulna styloid processes while the wrist is held in the neutral, supinated, and pronated positions. The computer may then eliminate the translation of these bones as they are moved from the computation to arrive at a true and accurate measure of the wrist's range of motion. Further information may also be obtained relating to the range of supination and pronation at the metacarpal level, which provide additional functional information of interest to the surgeon. However, perhaps the greatest advantage of the device is that it dramatically reduces the amount of therapists' time required to perform the clinical evaluation, and virtually eliminates the hand surgeon's time in evaluating the therapists' results. This is all achieved while significantly increasing the reliability and variability of the results.

Briefly, the protocol for entering data corresponding to the hand includes locating twenty-four specific points on the dorsal surface of the hand in a sequence which permits the most rapid data collection as well as to give maximum flexion values. As can be appreciated, this protocol can be routinely performed by an average therapist in less than two minutes. Data entry is achieved by touching the finger or hand with a wand or pointer, and pressing a foot switch when the wand or pointer is in the appropriate and desired location. This permits the therapist to choose the point in time for data entry to provide greater control over the evaluation.

A software package which operates on the control desktop personal microcomputer has been designed and developed by the inventors which guides and instructs the therapist as he/she proceeds through the evaluation process. This ensures a complete examination taken with the same methodology and helps improve the accuracy of results. In the prior art, significant inconsistencies of results are often noticed between therapists examining the same patient. With the present invention, these inconsistencies are thought to be significantly reduced. Furthermore, the software calculates angles of flexion and extension from the position data entered by the therapist and makes further calculations in accordance with AMA standards to arrive at the degree of disability. A hand surgeon may then review these results and verify them in accordance with accepted medical practice. However, because of the increased reliability brought to the measurement and data entry portions of the evaluation, the amount of time and involvement of the hand surgeon can be significantly reduced thereby significantly reducing the cost of the evaluation to the patient while improving the results obtained thereby.

As described above, the assignee's prior patented Upper Extremity Evaluation System is a dramatic improvement over the prior art. However, data is input to the device using a three-dimensional spatial absolute position sensor to locate the (x, y, z) coordinates of a series of points in space which correspond to particular points on a patient's hand. This methodology is useful and valuable, however, it does not represent a direct angular measurement of the range of motion of a joint utilizing the three orthogonal coordinates of motion generally permitted in many joints.

For purposes of explaining the principles and object of the present invention, the wrist will be used as an example. However, it should be understood that the present invention may be applied to any joint of the body and is particularly valuable and useful with respect to a joint permitting three degrees of freedom such as the wrist. As is well known, the hand may be moved in a generally horizontal plane which corresponds to an aximuth angle of movement through the wrist. Also, the hand may be moved generally in a vertical plane which corresponds to an elevational angular deflection in the wrist. Lastly, the hand may be rotated about the wrist to expose the palm upwardly and downwardly which generally corresponds to axial angular deflection through the wrist. These angular deflections, and their range of motion, are exactly the data of interest to be collected in determining the range of motion of the wrist for clinical purposes.

The same three-dimensional position and orientation device disclosed in the assignee's prior U.S. Pat. No. 4,922,925 referenced above includes sensors which can be used to measure Euler angles about a common source. This data is available in addition to the (x, y, z) data which is the subject of the prior patent mentioned herein. In order to more closely measure the actual angular deflection through a joint such as the wrist, the inventors herein have succeeded in designing and developing a joint evaluation system which utilizes the Euler angle information available with this system for directly measuring the angular deflection and hence range of motion of the joint. By utilizing Euler angles, and by directly positioning the sensors on the hand, variations in measurement caused by a therapist collecting data corresponding to inconsistent locations on the knuckles, or which might be caused by partially frozen joints which alter the normal path of movement of a joint are eliminated. Furthermore, not only are these variations eliminated, but close and accurate tracking of abnormal movements with electronically collected data is for the first time possible. This is because any cocking or tilting of one side of the joint with respect to the other as the joint is moved is readily indicated by a corresponding change in at least one of the Euler angles. As particular points are utilized in the assignee's prior patented system, variations from the norm in joint movement are not necessarily detected or indicated from the collected data. Thus, the system of the present invention which utilizes Euler angles (azimuth, elevation, roll) and a direct comparison of Euler angles to determine joint movement, represents an ability to collect data having still more accurate information with respect to the particular joint movement under evaluation. Thus, the present invention provides certain advantages over the system disclosed in U.S. Pat. No. 4,922,925.

While the principal advantages and features of the present invention have been briefly described, a fuller understanding may be attained by referring to the drawings and description of the preferred embodiment which follow.

DETAILED DESCRIPTION OF THE PREFERRED EMBODIMENT

Figure 1:
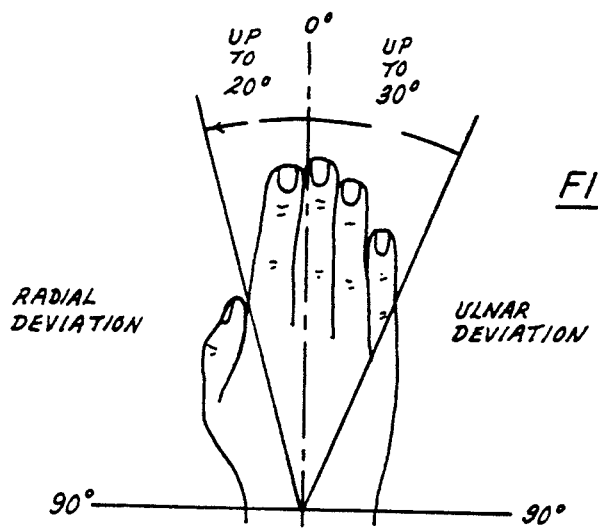
FIG. 1 is a top view of a hand depicting radial-ulnar deviation.

As shown in FIG. 1, radial deviation and ulnar deviation are defined as the motion of the wrist joint that results in the hand moving toward the radius and ulna bones, respectively. In other words, as shown in FIG. 1, movement of the hand to the left or to the right results in either radial or ulnar deviation from a neutral position defined along the approximate center line of the hand and aligned with the third metacarpal (not shown). As shown in FIG. 1, normal motion of the wrist for radial deviation is 20° and 30° for ulnar deviation. Movement in this direction corresponds to movement through an azimuth angle, the azimuth angle corresponding to one of the Euler angles.

Figure 2:
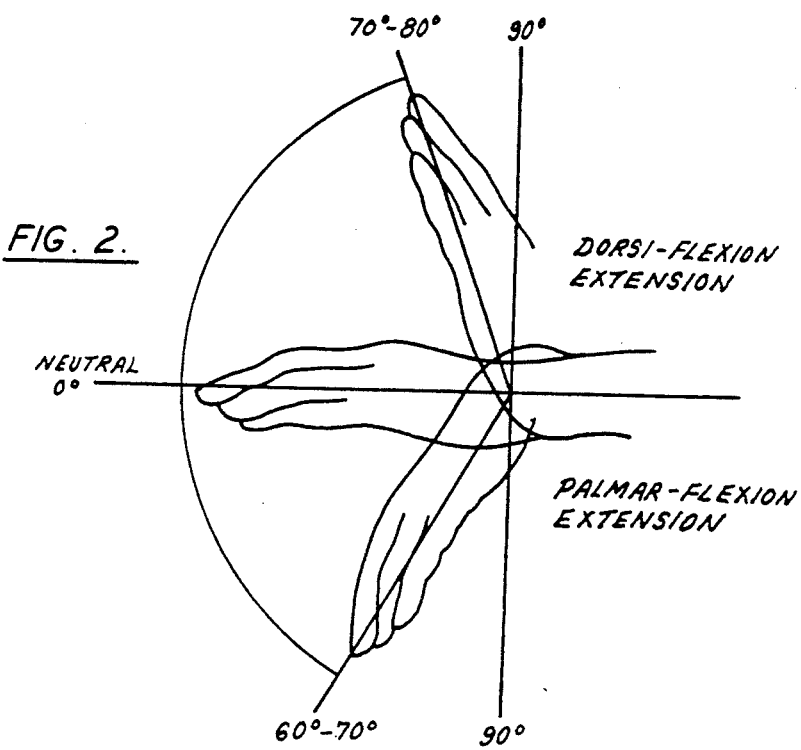
FIG. 2 is a side view of the hand depicting flexion-extension.

Referring now to FIG. 2, the hand is shown from the side view to illustrate the second major motion of the wrist as flexion and extension. Movement of the hand toward its palmar surface is defined as flexion, while movement toward the dorsal surface is defined as extension. As shown in FIG. 2, the average range of motion is 65° for flexion and 75° for extension. The flexion-extension movement of the hand corresponds to an angular movement through the wrist in an elevation angle, one of the Euler angles.

Figure 3:
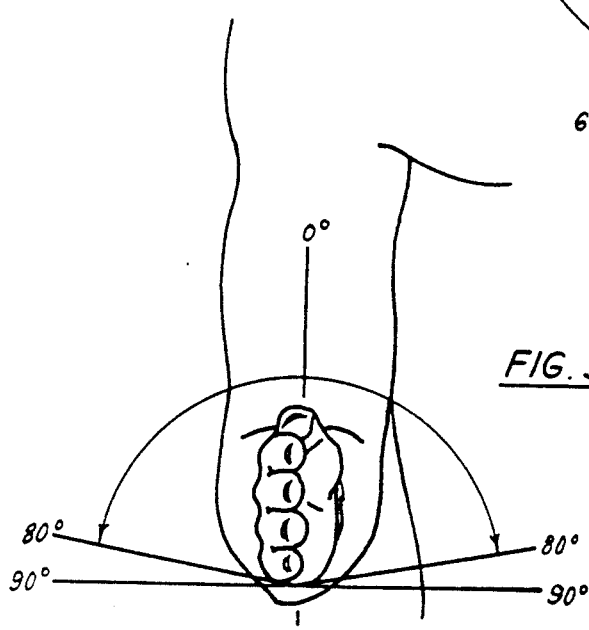
FIG. 3 is a front view of a hand and forearm depicting supination and pronation.

Referring now to FIG. 3, the hand and forearm are shown aligned at substantially 90° with the upper arm with the hand also aligned at substantially 90° with a flat surface which supports it. This position illustrates the third independent motion of the wrist which is supination and pronation. This motion is the twisting of the wrist about the longitudinal axis of the forearm. While this motion actually takes place in the forearm rather than the wrist joint itself, it is measured in all wrist motion evaluations. Supination is defined as the rotary motion of the forearm which results in the palm facing up, while pronation is movement in the opposite direction with the palm facing down. The average range of motion is approximately 80° in either direction. For our purposes, movement in the supination-pronation direction is defined as roll or movement about the central axis of the forearm, an Euler angle also.

Figure 4:
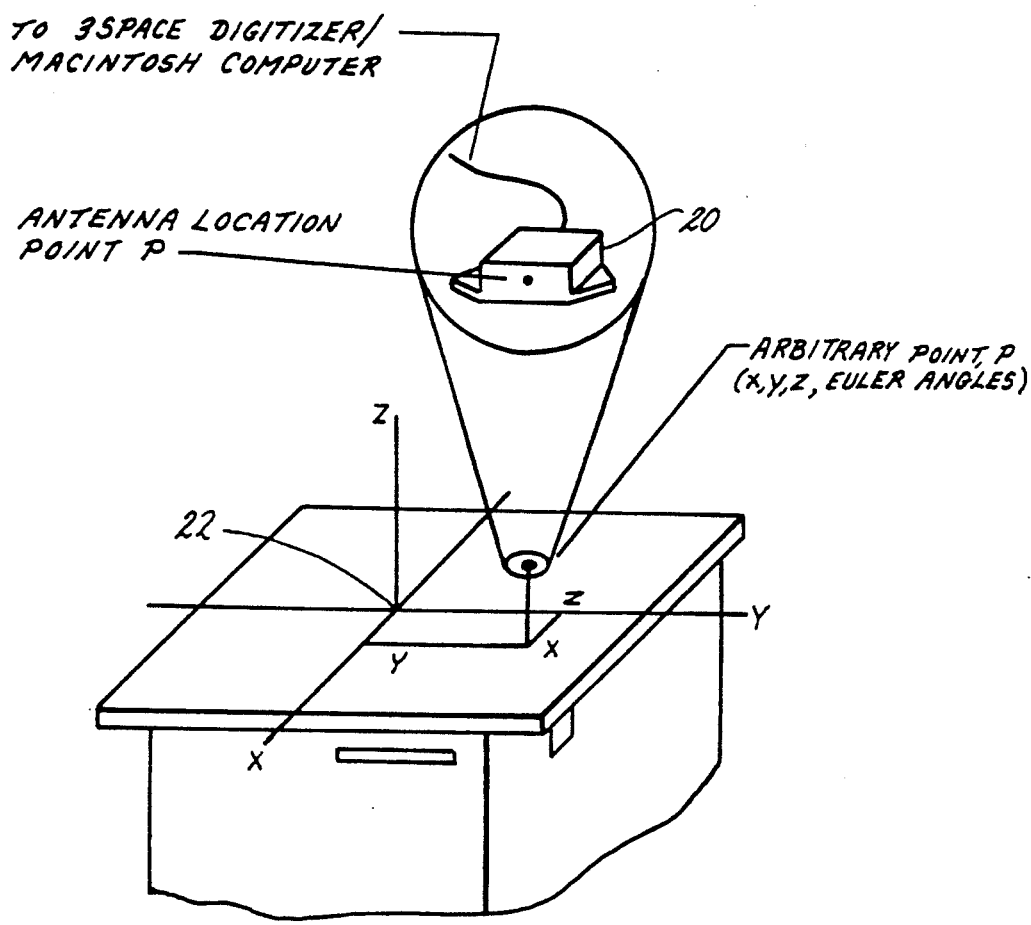
FIG. 4 is a perspective view of the three space digitizer and an associated antenna.

As shown in FIG. 4, a three space digitizer-tracker as is available from the Polhemus Navigation Sciences Division of McDonnell Douglas Electronics Company is used to generate the Euler angles of interest in the present invention. As shown in FIG. 4, an antenna 20 has a position point P and also an orthogonal coordinate system (x, y, z) which corresponds to the x, y, z coordinate system of the source 22. Any difference in alignment between any two of the x, y, or z axes will result in an output corresponding to an Euler angle indicative of that misalignment or canting. Thus, the orientation of sensor 20 within the field is obtained by knowing the orientation angles of the sensor's 20 coordinate system with respect to the coordinate system of the source 22. This is all as well known with respect to the three space digitizer.

Figure 5:
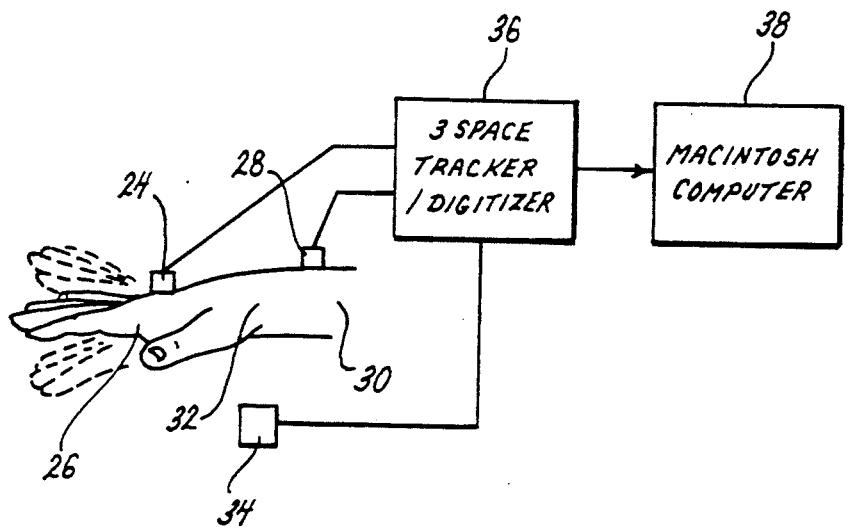
FIG. 5 is a diagrammatic view of a patient's hand with sensors secured thereto and connected to the system of the present invention.
Figure 6:
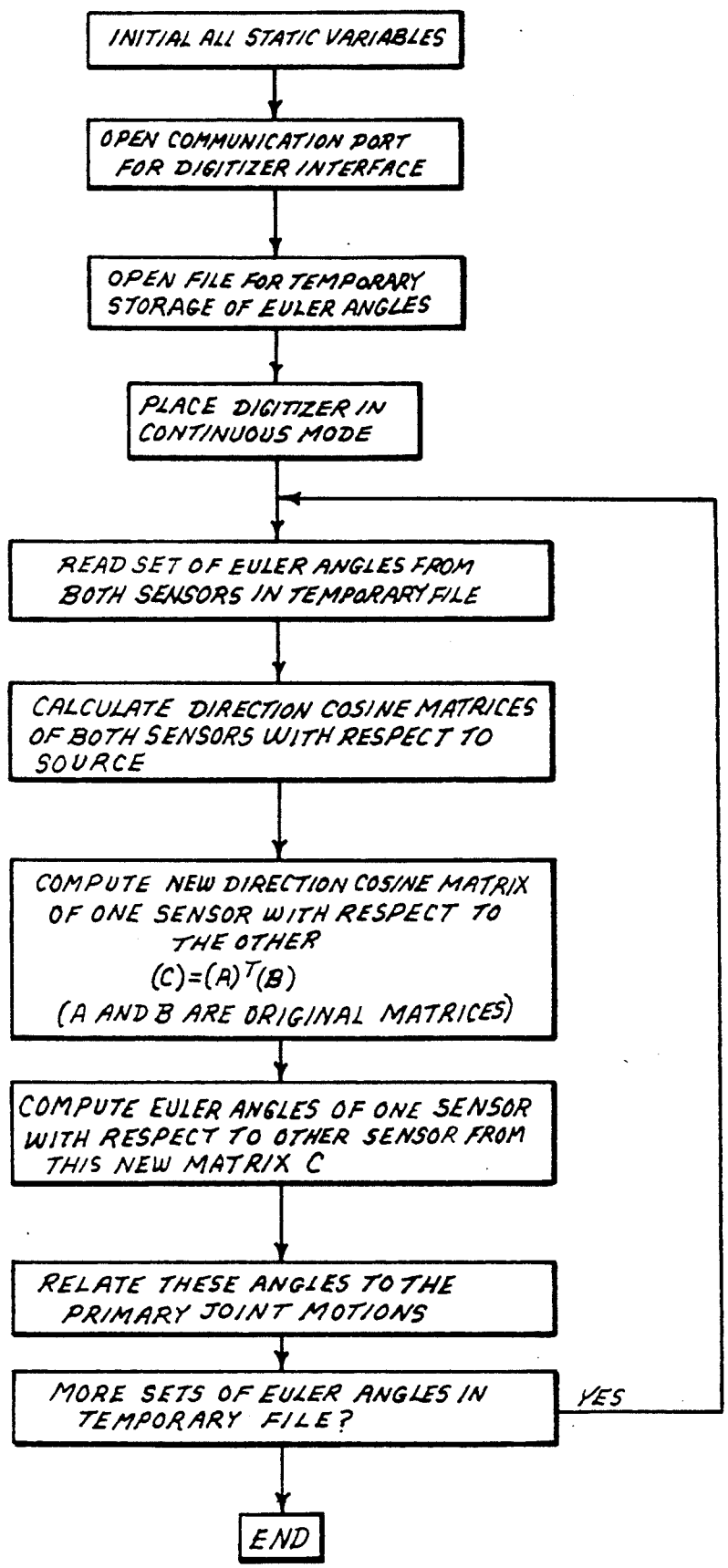
FIG. 6 is a flow chart explaining the processing of Euler angle information to determine angular movement of a joint.

As shown in FIG. 5, a first sensor 24 may be mounted to the dorsal surface of the hand 26 and aligned to coincide with the neutral position as shown in FIGS. 1-3. A second sensor 28 may be mounted on the forearm 30 such that sensor 24 is distal and sensor 28 is proximal to the wrist 32. Although not shown, multiple sensors could be used on multiple joints. A source 34 is also provided as part of the three space tracker/digitizer 36, as is known. The output of the three space tracker/digitizer 36 is communicated to a computer such as a MacIntosh computer 38 for analysis of the data in accordance with the flow chart of FIG. 6.

As shown in FIG. 5, movement of the hand 26 about the forearm 30 (corresponding to angular deflection through the wrist joint 32) results in the generation of one set of Euler angles for sensor 24 and another set of Euler angles for sensor 28, both with respect to source 34. The three space tracker/digitizer 36 generates this Euler angle information to MacIntosh computer 38 which then further processes the data to compute Euler angles of one sensor with respect to the other sensor. Presuming that sensors 24, 28 have been properly aligned with the neutral positions for the wrist in all three of its orthogonal ranges of motion, then the difference in Euler angles between sensors represents the range of movement of the wrist. Thus, in accordance with the principles of the present invention, direct angular measurement of the wrist is permitted and is continuously monitored in all three of the orthogonal permitted movements of the wrist to thereby automatically detect and collect data which would be indicative of both normal or abnormal movement. The information can be collected either statically or dynamically with the hand moved and held at the extremes of motion, or as the hand is moved through the range of its movement. Furthermore, as described herein, the present invention does not utilize position or (x, y, z) data which requires a therapist to select particular points along the hand or wrist to achieve a measurement thereof.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. In an electronic device having means for measuring the range of motion of a wrist, said wrist permitting angular movement through a plurality of orthogonal planes, said orthogonal planes comprising a substantially azimuthal plane corresponding to radial-ulnar deviation, a substantially elevational plane corresponding to flexion-extension, and a substantially axial plane aligned with the forearm corresponding to supination-pronation, the improvement comprising sensor means for directly, electronically measuring the angular range of motion of said wrist through each of said orthogonal planes of movement, said sensor means having means for generating an output comprised of angular data relating to said wrist, and means for measuring angular movement through more than one of said orthogonal planes at the same time, said sensor means comprising a pair of sensors, each of said sensors being adapted for placement on opposite sides of said wrist, the device having means for detecting a change in angular orientation with respect to each of said sensors from a common source.

2. The device of claim 1 including means for directly sensing the angular orientation of each sensor with respect to the source in terms of its Euler angles.

3. The device of claim 2 including means for comparing the Euler angles of one sensor with the Euler angles of the other sensor and thereby arriving at the angle of movement through each of said orthogonal planes of movement.

4. The device of claim 3 wherein the sensors, when applied to said wrist, are substantially aligned with said wrist so that each sensor coordinate system is aligned with the wrist's orthogonal planes of movement.

* * * * *